United States Patent [19]

Heinecke

[11] E Patent Number: Re. 33,353

[45] Reissued Date of Patent: Sep. 25, 1990

[54] THIN FILM SURGICAL DRESSING WITH DELIVERY SYSTEM

[75] Inventor: Steven B. Heinecke, New Richmond, Wis.

[73] Assignee: Minnesota Mining and Manufacturing Company, St. Paul, Minn.

[21] Appl. No.: 359,833

[22] Filed: May 31, 1989

Related U.S. Patent Documents

Reissue of:

[64] Patent No.: 4,598,004
Issued: Jul. 1, 1986
Appl. No.: 695,042
Filed: Jan. 24, 1985

[51] Int. Cl.[5] ..... C09J 7/02; A61F 13/02

[52] U.S. Cl. ..... 428/40; 128/156; 428/41; 428/131; 428/132; 428/137; 428/192; 428/343; 428/352; 428/354; 428/914

[58] Field of Search ..... 428/378, 40, 914, 192, 428/343, 136, 352, 132, 137, 354, 41; 128/155, 156

[56] References Cited

U.S. PATENT DOCUMENTS

| | | | |
|---|---|---|---|
| 3,645,835 | 2/1972 | Hodgson | 128/156 X |
| 4,080,969 | 3/1978 | Casey et al. | 428/378 X |
| 4,413,621 | 11/1983 | McCracken | 128/156 |
| 4,414,970 | 11/1983 | Berry | 128/156 |
| 4,420,519 | 12/1983 | Slemmons | 428/40 |
| 4,513,739 | 4/1985 | Johns | 128/156 |

FOREIGN PATENT DOCUMENTS

| | | | |
|---|---|---|---|
| 81304905 | 10/1981 | European Pat. Off. . | |
| 0051935 | 5/1982 | European Pat. Off. | 428/914 X |
| 84300752.7 | 2/1984 | European Pat. Off. . | |
| 0120570 | 10/1984 | European Pat. Off. | 128/156 |

*Primary Examiner*—Thomas J. Herbert
*Attorney, Agent, or Firm*—Donald M. Sell; Walter N. Kirn; Dale A. Bjorkman

[57] ABSTRACT

A pressure sensitive adhesive composite with a delivery system having particular benefit in application of very thin backings such as high moisture vapor permeable films widely used as medical dressings is disclosed. The composite has a backing coated with adhesive on at least a portion of the backing and liner over the adhesive. At least one edge of the backing is a delivery strip which is separable from the remainder of the backing. The liner is securely adhered to the delivery strip and releaseably adhered to the remainder of the adhesive coated backing. The bond between the a liner and the delivery strip is strong enough that the delivery strip will separate from the remainder of the backing before it will separate from the liner.

11 Claims, 2 Drawing Sheets

THIN FILM SURGICAL DRESSING WITH DELIVERY SYSTEM

Matter enclosed in heavy brackets [ ] appears in the original patent but forms no part of this reissue specification; matter printed in italics indicates the additions made by reissue.

FIELD OF INVENTION

The present invention relates to pressure sensitive adhesive (PSA) composites comprising a backing coated on at least one side with adhesive. More particularly it relates to a PSA composite having a delivery system to aid placing the composite on a surface. The invention is of particular benefit in applications of very thin films such as the high moisture vapor permeable films widely used as medical dressings.

BACKGROUND

Although the present invention is useful in any adhesive composite needing a delivery system, it has particular benefit in connection with transparent film dressings and surgical drapes. These dressings and drapes are widely used as a protective layer over a wound, facilitating healing in a moist environment while acting as a barrier to liquids and bacteria. Dressings of this type are available under trade names such as Tegaderm TM (3M, St. Paul, MN) Bioclosure TM (Johnson & Johnson, New Brunswick, N.J.) and Op-Site TM T. J. Smith & Nephew, Hull, England). Uniflex TM (Howmedica, Largo, Fla.), U.S. Pat. No. 3,645,835, which is hereby incorporated by reference, describes one such moisture vapor permeable, water bacteria impermeable dressing.

The polymeric films used in such dressings are extremely thin, flimsy, and supple. They are supplied with a releasable protective liner overlying the adhesive coated surface of the film. When the liner is removed the adhesive coated film tends to fold and stick to itself forming wrinkles which render smooth aseptic application of a dressing or drape to skin very difficult. Various delivery systems have been proposed to obviate this problem.

One such delivery system utilizes a frame to support the edges of the film during its application. European Pat. Appln. No. 81 30 4905 describe a composite having a relatively thin polymeric film which is conformable to animal anatomic surfaces. A pressure sensitive adhesive is coated to at least a portion of one surface of the polymeric film. A release liner is attached to the adhesive coated surface of the film. A second releasable layer or carrier is attached to the opposing (exposed) surface of the film. This second releasable layer is attached to the film more tenaciously than the release liner is adhered to the adhesive side of the film and is preferably a frame adhered to the periphery of the film. In use the releasable layer stays with the film until the film is affixed to the substrate, at which time it may be removed.

Another delivery system is utilized in the Op-Site TM dressing. In that dressing the film is provided with a pull tab along one edge of the film. The releasable liner is removed by peeling the liner and the pull tab away from each other. The pictorial instructions supplied with the product suggest that the dressing should be applied by grasping the pull tab and the releasable liner which has been partially removed and then placing the film on the intended site. Thereafter the releasable liner is completely peeled off and the dressing smoothed to the skin surface. The pull tab can be left in place or, in an alternative embodiment, the pull tab and the film to which it is adhered are removed from the remainder of the dressing by separation along perforations provided for this purpose. U.S. Pat. No. 4,413,621 describes such a dressing.

A third delivery system is described in European Pat. Appln. No. 84 30 0752.7 (publication No. 0,120,570). That application describes a wound dressing made of a film that is coated on one face with a biocompatible adhesive. One or more liner sheets are releasably adhered to the adhesive coated surface. Release retarding means are provided along one edge or a pair of opposed edges of the dressing to require a greater force to separate the layers (film, adhesive, and liner) at the edge or edges than at the remainder of the contact area. The release retarding means may be a thicker strip of the polymeric film, a stiffer piece of film adhered to the film at its edges, a strip of liner backing wrapped around the edge of the film and adhered to the surface of the film, or a strip attached to the exposed surfaces of both the film and the backing. Alternatively an adhesive having greater tenacity than the quick release adhesion of the biocompatible adhesive for the liner may be used.

SUMMARY OF THE INVENTION

The adhesive composite of the present invention has three layers—a backing, a pressure sensitive adhesive layer coated on at least a portion of one surface of the backing, and a liner over the adhesive. At least one edge of the backing is a delivery strip which is separable from the remainder of the backing. The liner is securely adhered to the delivery strip portion of the adhesive-coated backing and it is releasably adhered to the remaining surface of the adhesive-coated backing. The bond between the liner and the delivery strip is strong enough that the delivery strip will separate from the remainder of the backing before it will separate from the liner.

The backing is preferably a film provided with perforations to define the delivery strip edge. In use pulling firmly on the liner which is adhered to the delivery strip of the film but which has been peeled back from the remaining areas of the film will cause the film to tear along the perforations.

The preferred adhesive coated film is permeable to moisture and vapor and should transmit moisture vapor at a rate of at least 300 g/m$^2$/24 Hrs/37° C./100–10% RH. Preferably the adhesive coated film transmits moisture vapor at a rate of at least 700 g/m$^2$/24 Hrs/37° C./100–10% RH. When a high moisture vapor permeable film is used the adhesive is preferably biocompatible. Most preferably the PSA composite comprises high moisture vapor permeable film, a biocompatible adhesive and is transparent.

The preferred method of securely attaching the liner to the delivery strip entails use of a conventional liner material which has been strip coated with a releasing agent, e.g. silicone. In the preferred embodiment the liner is left free of any releasing agent along the strip that contacts the delivery strip of the film. The remaining surfaces of the liner, that is those areas that will releasably contact the PSA coated film, are coated with the releasing agent. In a composite of this type, the adhesion of the liner to the pressure sensitive adhesive coated on the delivery strip may be increased by irradiation. Adhesives which increase their adhesion upon irradiation are known in the art. When the adhesive is a copolymer of iso-octylacrylate and acrylamide irradiation to increase adhesion can take place simultaneously with sterilization when gamma irradiation is used.

The adhesive composite of the present invention may be constructed with two delivery strips at opposing edges of the film. In this embodiment the liner is comprised of at least first and second segments wherein the first segment is adhered to one delivery strip and the second segment is adhered to the opposing delivery strip. Preferably in this embodiment the two segments of the liner are releasably adhered to the adhesive coated film and meet near the center of the film. They are preferably provided with an extension of liner material to facilitate peeling of the liner segments. These extensions may be integral with the liner or separate pull handles adhered to the liner. They may be folded in a conventional "J" fold. Alternatively one piece of liner can be folded in a "J" fold while the continuing surface of the second piece of liner extends beyond the "J" fold of the first.

In an alternative embodiment the film has one delivery strip at one edge and the liner extends across the entire adhesive-coated surface of the film. In this embodiment the film is preferably provided with a pull tab at the edge opposing the delivery strip edge of the film. In use the pull tab may be left in place after application of the film, or the pull tab may be releasably adhered to the film and removed after application of the film. In this latter alternative the pull tab should adhere to the film with greater tenacity than the adhesion of the releasable portions of the liner.

In the method of this invention a thin flexible adhesive coated film is applied to a substrate wherein the film has a delivery strip along at least one edge thereof which strip is a separable from the remainder of the film and a liner is adhered to the adhesive coated surface of the film which liner is adhered to the delivery strip of the film with sufficient tenacity to result in separation of the delivery strip from the remainder of the film before the liner-delivery strip bond fails and which liner is releasably adhered to the skin contacting surface of the film. The composite is applied by removing the liner from the substrate contacting surface of the film, placing the substrate contacting surface of the film into intimate contact with the intended site, and thereafter separating the liner and delivery strip from the film.

DETAILED DESCRIPTION

Figure 1:
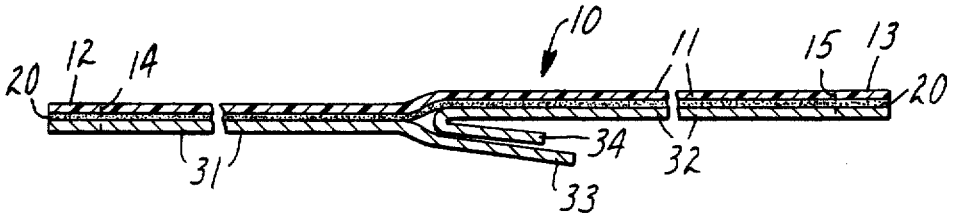
FIG. 1 is a cross sectional view of the adhesive composite of the present invention.

The delivery system of the present invention is useful in connection with any backing having a pressure sensitive adhesive coated on to it. Representative backings include nonwoven fibrous webs, fibrous film webs, knits, and other familiar backing materials. The preferred backing materials are polymeric films. The invention is particularly useful in PSA composites having high moisture vapor permeable films. U.S. Pat. No. 3,645,835 describes a method of making such a high vapor/moisture permeable film and a method for testing its permeability.

The film is also preferably conformable to body surfaces. Generally the films are from 12 to 25 microns thick. Conformability is somewhat dependent on thickness, thus the thinner the film the more conformable it is. In the preferred embodiment the films used in the device of the present invention are conformable to animal anatomical surfaces. This means that when the film is applied to an animal anatomical surface it conforms to the surface even when the surface is moved. The preferred films are conformable to animal anatomical joints. When the joint is flexed and then returned to its unflexed position, the film stretches to accommodate the flexion of the joint but is resilient enough to continue to conform to the joint when the joint is returned to its unflexed condition. A measure of conformability is the $F_{10}$ modulus. The $F_{10}$ modulus should be no greater than about 1 pound (454 grams) and preferably less than about 0.8 pounds (363 grams). In the preferred embodiments of wound dressings and drapes, films which have $F_{10}$ moduli upwards of 2.5 pounds (1135 grams) may be used. However, as the $F_{10}$ modulus increases the conformability decreases and the ability of the film to perform comfortably as medical dressings likewise decreases.

$F_{10}$ modulus as referred to herein is effectively determined using an Instron Unit Model 1102 from Instron Corp., 2500 Washington Street, Canton, Mass. The cross-head speed of the Instron is set at ten inches per minute and the chart speed is set at ten inches (25.4 cm) per minute. The gauge length is set at two inches (5 cm) with the test sample cut to test a one-inch width (2.54 cm).

Examples of polymers which are suitable for use as wound dressing films in the present invention include polyurethane, elastomeric polyester such as DuPont "Hytrel" polyester elastomer (Wilmington, Delaware), polyethylene, blends of polyurethane and polyester, chlorinated polyethylene, styrene/butadiene block copolymers such as "Kraton" brand thermoplastic rubber (Shell Chemical Company, Houston Tex.), and polyvinyl chloride.

Particularly preferred films are polyurethane and elastomeric polyester films. These films combine the desirable properties of resiliency, high moisture vapor permeability and transparency.

The preferred adhesives which can be used in the preferred wound dressing embodiment are the normal adhesives which are applied to the skin such as those described in U.S. Pat. No. Re. 24,906, particularly a copolymer of 96% iso-octyl acrylate units and 4% acrylamide units and a copolymer of 94% iso-octyl acrylate units and 6% acrylic acid units. Other useful adhesives are those described in U.S. Pat. No. 3,389,827 which comprise block copolymers having three or more polymer block structures having a general configuration —A—B—A— wherein each A is a thermoplastic polymer block with a glass transition temperature above room temperature (i.e., above about 20° C.) having an average molecular weight between about 5000 and 125,000 and B is a polymer block of a conjugated diene having an average molecular weight between about 15,000 and 250,000. Additional examples of useful adhesive are iso-octyl acrylate/n-vinyl pyrrolidone copolymer adhesives and crosslinked acrylate adhesives such as for example those described in U.S. Pat. No. 4,112,213. Inclusion in the adhesive of medicaments or antimicrobial agents such as iodine is useful for enhancing wound healing and preventing infection. U.S. Pat. Nos. 4,310,509 and 4,323,557 describe antimicrobial adhesives.

The liner is preferably strip coated with a releasing agent applied to the liner only in the areas which will contact the substrate (e.g. the skin contacting surface of the film). No release agent is applied to the strips which will contact the delivery strips of the film. Examples of liners suitable for use in the present invention are strip coated liners made of kraft papers, polyethylene, polypropylene or polyester, and are coated with releasing agents such as fluorochemicals or silicone. U.S. Pat. No. 4,472,480 describes low surface energy perfluorochemical liners. The preferred liners are silicone coated release papers, polyolefin films, or polyester films. Examples of the silicone coated release papers are Polyslik TM silicone release papers supplied by H. P. Smith Co., Chicago, Ill. and silicone coated papers supplied by Daubert Chemical Co., Dixon, Ill. The preferred liner is 75-W-89-SPT3A-Zoned/PST3A paper available from Schoeller Release Products, West Chicago, Ill. This products is a polyethylene coated kraft paper bearing an electron beam cured silicone surface. The silicone is coated in the areas which are releasably adhered to the substrate (e.g., skin) contacting surface of the film and uncoated in the areas which are adhered to the delivery strips of the film.

Other combinations of adhesive and liner are feasible. Those skilled in the art are familiar with process of testing a new adhesive against different liners, or a new liner against different adhesives in order to arrive at the combination of qualities desired in the final product. Handbook of Pressure-Sensitive Adhesive Technology, Chapter 18 "Silicone Release Coatings"Van Nostrand-Reinhold, 1982, pp. 384–403, which is hereby incorporated by reference describes the considerations pertinent to selection of a silicone release liner. U.S. Pat. No. 4,472,480 which is hereby incorporated by reference describes considerations pertinent to selection of a perfluoropolyether liner. In the preferred wound dressing embodiment of the present invention, the choice of adhesive is limited to those that are safe to use on skin, and preferably to those that are of the class known as hypollergenic. The preferred polyacrylates are adhesives of this class. Liners are available from a variety of manufacturers in a wide variety of proprietary formulations. One normally tests these in simulated use conditions against an adhesive of choice to arrive at a product with the desired release characteristics.

In the present invention, a parameter in addition to selection of the adhesive, the liner, and the method of fixation can be varied to achieve the desired tenacity of adhesion of the liner to the delivery strip. This factor is the perforations or line of weakness put into the film to allow breakage of the delivery strip from the remainder of the film. For example, after the combination of adhesive and liner which give the desired low peel force when removing the liner is selected a pattern of perforations is developed, which is found to hold when the film is gently held taut while being applied, but which breaks when a slightly greater pull is applied by the user. Too few perforations will result in a film which stretches, deforms, and tears unevenly. Too many or too large perforations will yield a film which tears to readily.

Figure 2:
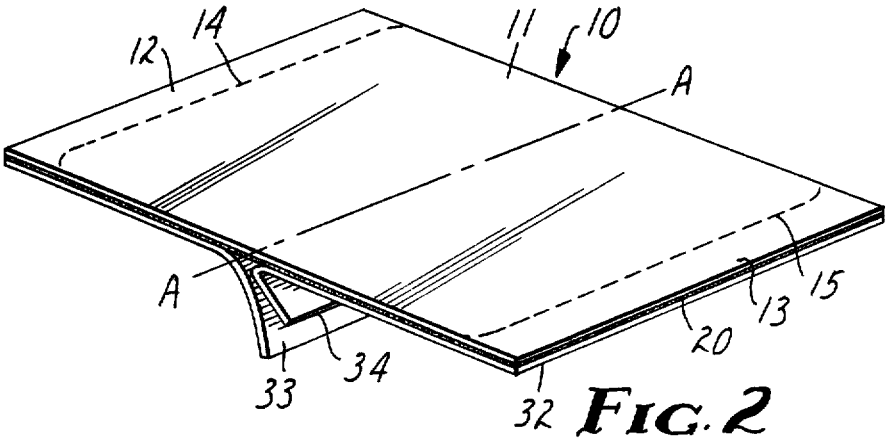
FIG. 2 is a perspective view of the adhesive composite of the present invention.
Figure 3:
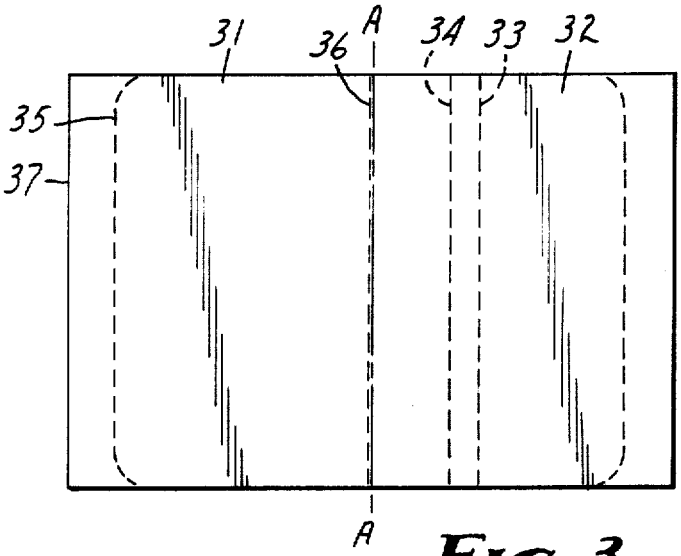
FIG. 3 is a plan view of the adhesive composite of the present invention showing the liner surface.

FIG. 1 shows the preferred embodiment of the present invention. This embodiment is a wound dressing 10 shown as received by the user. For clarity, protective and sterile outer wrappings are not shown. The dressing is made of a thin transparent, polymeric film 11 which is moisture vapor permeable, liquid and bacteria impermeable such as a polyester or polyurethane film. A coating of biocompatible pressure sensitive adhesive 20 such as non-allergenic polyacrylate bioadhesive covers the lower, skin contacting surface of the film. A liner in two segments 31 and 32 covers the adhesive. The two segments meet near the center of the dressing and are provided with integral extensions 33 and 34 which serve as handles to be grasped by the user when removing the liner segments. One extension 33 is virtually flat; the other extension 34 is shown folded in a "J" pattern. At the two opposed edges of the film 11 are delivery strips 12 and 13. The delivery strips 12 and 13 are defined by the edges of the film and the perforation lines 14 and 15. The liner segments 31 and 32 are firmly adhered to the adhesive coated delivery strips 12 and 13. This affixing may be accomplished in several ways. The fixation may be mechanical. A heat sea may be used. Another way is to have the liner strip coated with a release agent (e.g. silicone). As best shown in FIG. 3, therefore liner 31 is coated with release agent in the portion defined by lines 35 and 36. The remaining portion of the liner (defined by lines 35 and 37) is left free of release agent. The portion which has no release agent is firmly adhered to the delivery strip 12, preferably by increasing the strength of adhesion between the adhesive coated delivery strip 12 and the liner by irradiation. In the preferred embodiment where the adhesive is a copolymer of isooctylacrylate and acrylamide, the bond between the delivery strip and the liner may be conveniently increased during sterilization of the product with gamma irradiation. The bond formed between the liner and the delivery strip is stronger than the line of weakness (e.g. perforations 14 and 15 best shown in FIG. 2) which permits separation of the delivery strip from the skin contacting surface of the film.

Figure 4:
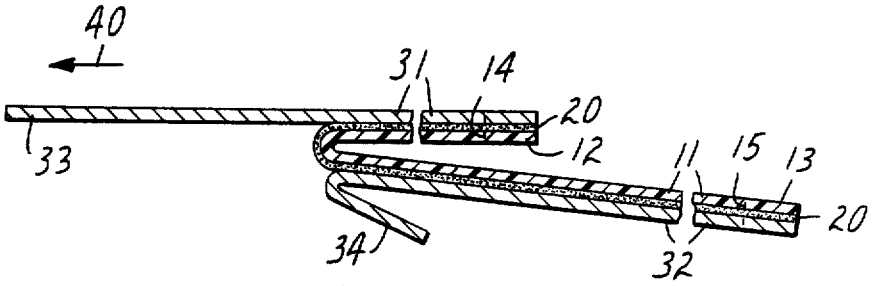
FIG. 4 is a cross section of view of the present invention showing separation of the releasable portions of the liner from an adhesive coated film.
Figure 5:
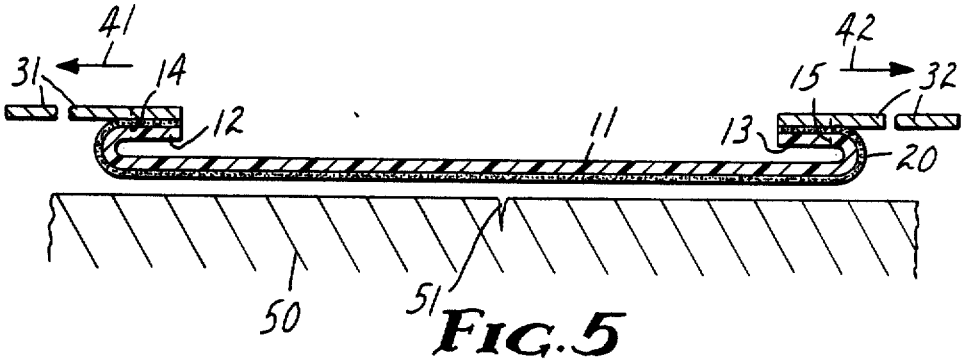
FIG. 5 is a cross section view of the present invention showing application of an adhesive coated film to a substrate.

FIG. 4 shows the dressing of FIG. 1 being prepared for application to a wound. For ease of illustration the dressing has been folded around line A—A shown in FIGS. 2 and 3. With the film 11 being extremely flexible and bent as shown in FIG. 4, and where the liner is chosen so as to have low adhesion of the liner to the film, liner segment 31 begins to peel off the adhesive coated film. When a gentle pull is applied to liner segment 31 as indicated by arrow 40, this peeling will continue until the entire segment 31 is peeled from the film except for the portion defined by lines 35 and 37 which is securely adhered to the delivery strip 12. With continued gentle pulling of the liner 31 the film will unfold and the other segment of the liner 32 will peel off the film until the condition shown in FIG. 5 is reached. Alternatively, the liner segments 31 and 32 may be peeled from the adhesive coated film simultaneously. When this procedure is employed the condition shown in FIG. 5 is similarly reached.

FIG. 5 shows the dressing 10 with the adhesive coated surface positioned for application the wound. Further increasing the tension applied to the skin 50 of a patient over a wound 51. The dressing is made taut by gentle tension applied in directions 41 and 42. It is then smoothed down onto the wound. Further increasing the tension applied to the film by pulling the liner segments will cause the film to break along perforation lines 14 and 15. After the film tears along the perforations 14 and 15 the film lies flat on the skin and, because of its physical characteristics, forms a homogeneous and unobtrusive dressing which conforms well to the contours of the skin. The liner and delivery strips are discarded.

Figure 6:
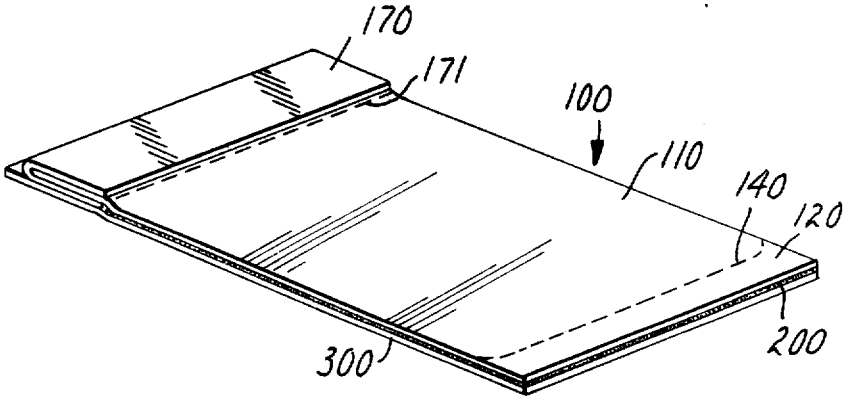
FIG. 6 is a perspective view of an alternative embodiment adhesive composite showing a composite with a unitary liner and a pull tab on the film.

FIG. 6 shows an alternative embodiment of the present invention. This embodiment, shown as a wound dressing 100, has a liner 300 formed as one segment. The dressing is made of a thin transparent, polymeric film 110 which is moisture vapor permeable and liquid and bacteria impermeable. A coating of biocompatible pressure sensitive adhesive 200 such as polyacrylate bioadhesive covers the lower skin contacting surface of the film. A liner 300 covers the adhesive. At one edge of the film is a delivery strip 120. The delivery strip is defined by the edge of the film and perforation line 140. At the opposite end of the film 110 is a pull tab 170. The pull tab 170 may be an extension of the film having no adhesive and without perforations, or it may have a perforation line 171 so that it can be removed after application of the dressing to the skin. The liner is firmly adhered to the delivery strip. The remaining portions of the liner is releasably adhered to the remainder of the film. To apply this dressing the user grasps the pull tab 170 and begins to peel the liner 300. Then holding the pull tab and liner the releasable portion of the liner is removed and the film is placed onto the intended site and smoothed. At this time a firm tug will cause the delivery strip to separate from the remainder of the film.

The composite of the present invention may be made by conventional techniques (e.g. extrusion, solvent casting, calendering, and laminating and the like) which are familiar to those skilled in the art. (See Modern Plastics Encyclopedia McGraw Hill, 1984–85; Coating and Laminating Machines, Weiss Converting Technology Co., 1977.) The method of making a composite is further exemplified by the following non limiting example.

EXAMPLE

Twenty five grams per square meter of an adhesive prepared in accordance with U.S. Pat. No. Re. 24,906, which is incorporated by reference, comprising of copolymer of 96% units of isooctylacrylate and 4% units acrylamide was applied to a release liner of 78 pounds (35412 grams) bleached, one-side coated, polyethylene and silicone paper (Polyslik S-8053, H. P. Smith, Chicago, Ill. utilizing a standard horizontal knife coater. A 1.1 mil (28 micron) film of "Estane 58309NAT022 polyurethane resin (B. F. Goodrich, Cleveland, Ohio) was laminated to the adhesive surface. This material was then slit to proper width to make the size dressing desired. The adhesive/film laminate was then removed from the S-8053 release liner and relaminated to the J folded and flat finished product release liner (75W-89SPT3A-Zoned/PST3A, Schoeller Release Products, West Chicago, Ill.) to form a roll of double liner bandage stock with non-silicone strip or each edge of roll. The perforating and slitting of the dressing to size were performed using a die-cutting/printing machine (Model 813, Series KZY223, Mark Andy, St. Louis, Mo.).

The foregoing description has been directed to particular preferred embodiments for purposes of illustration and explanation. Those skilled in the art will appreciate that many modifications will be possible without departing from the spirit of the invention. For example the composite may further comprise a gauze dressing or the pressure sensitive adhesive may be pattern coated to increase moisture vapor transmission rate and decrease pain upon removal of a dressing. The following claims are intended to be interpreted to embrace all such modifications and variations.

What is claimed is:

1. An adhesive composite comprising a backing wherein at least one edge of the backing is a delivery strip which is separable by perforations from the remainder of the backing;

a pressure sensitive adhesive coated on at least a portion of one surface of the backing; and a liner which is adhered to the delivery strip with sufficient tenacity to result in separation along the perforations of the delivery strip from the remainder of the backing before the liner separates from the delivery strip and which liner is releasably adhered to the remainder of the backing, *wherein the liner is strip coated with releasing agent such that the portion contacting the delivery strip is free of releasing agent and the portion contacting the remainder of the film has releasing agent.*

2. The composite of claim 1 wherein the backing is a polymeric film.

3. The adhesive composite of claim 2 wherein the adhesive coated film has moisture/vapor transmission rate of at least 300 g/m$^2$/24 hrs/37° C./100–10% RH and the adhesive is biocompatible.

4. The adhesive composite of claim 3 wherein the film is transparent.

[5. The adhesive composite of claim 2 wherein the liner is strip coated with releasing agent such that the portion contacting the delivery strip is free of releasing agent and the portion contacting the remainder of the film has releasing agent.]

6. The adhesive composite of claim [5] *1* wherein the releasing agent is silicone.

7. The adhesive composite of claim [5] *1* wherein the adhesion of the pressure sensitive adhesive coated on the delivery strip to the liner is increased by irradiation.

8. The adhesive composite of claim 7 wherein the pressure sensitive adhesive is a copolymer of iso-octylacrylate and acrylamide.

9. The adhesive composite of claim 2 wherein the film has two delivery strips at opposing edges of the film and the liner is comprised of at least a first segment and a second segment wherein the first segment is adhered to one delivery strip and the second segment is adhered to the opposing delivery strip.

10. The adhesive composite of claim 2 wherein the film has a delivery strip at one edge and pull tab at the opposing edge.

11. The adhesive composite of claim 10 wherein the pull tab is releasably adhered to the film with greater tenacity than the adhesion of releasable portions of the liner.

12. A method of applying a thin flexible adhesive coated film to a substrate wherein the film has a delivery strip along at least one edge thereof which is separable from the remainder of the film and a liner adhered to the adhesive-coated surface of the film which liner is adhered to the delivery strip portion of the film with sufficient tenacity to result in separation of the delivery strip from the remainder of the film before the liner-delivery strip bond fails and which is releasably adhered to the remainder of the film, *wherein the liner is strip coated with releasing agent such that the portion contacting the delivery strip is free of releasing agent and the portion contacting the remainder of the film has releasing agent,* comprising:

removing the liner from the substrate contacting surface of film;

placing the substrate contacting surface in intimate contact with the skin; and separating the liner and delivery strip from the film.

* * * * *

UNITED STATES PATENT AND TRADEMARK OFFICE

CERTIFICATE OF CORRECTION

PATENT NO. : RE 33,353

DATED : September 25, 1990

INVENTOR(S) : Steven B. Heinecke

It is certified that error appears in the above-identified patent and that said Letters Patent is hereby corrected as shown below:

Col. 5, line 30, "products" should be — product —.

Col. 5, line 52, "hypollergenic" should be — hypoallergenic —.

Col. 6, line 4, "to" should be — too —.

Title Page:
Abstract, line 11, delete "a" between the words "the" and "liner".

Signed and Sealed this

Twenty-fifth Day of August, 1992

*Attest:*

DOUGLAS B. COMER

*Attesting Officer*

*Acting Commissioner of Patents and Trademarks*